United States Patent [19]
von Sturm et al.

[11] 3,941,135
[45] Mar. 2, 1976

[54] PACEMAKER WITH BIOFUEL CELL

[75] Inventors: Ferdinand von Sturm; Gerhard Richter, both of Erlangen, Germany

[73] Assignee: Siemens Aktiengesellschaft, Munich, Germany

[22] Filed: Mar. 24, 1975

[21] Appl. No.: 561,337

[30] Foreign Application Priority Data
Mar. 29, 1974  Germany............................ 2415385

[52] U.S. Cl. ........ 128/419 PS; 128/404; 128/419 B; 128/419 P; 136/86 F
[51] Int. Cl.² .......................................... A61N 1/36
[58] Field of Search .... 128/404, 418, 419 B, 419 P, 128/419 PG, 419 PS, 421, 422, 423; 136/86 DD, 86 F, 86 R

[56] References Cited
UNITED STATES PATENTS

| | | | |
|---|---|---|---|
| 3,421,512 | 1/1969 | Frasier............................ | 128/419 PS |
| 3,842,843 | 10/1974 | Mourot et al. ................ | 128/419 PS |

OTHER PUBLICATIONS

Schaldactt et al. "Transactions of the American Society for Artificial Internal Organs", Vol. XVI, 1970, pp.184–192.
Drake et al., "Transactions of the American Society for Artificial Internal Organs", Vol. XVI, 1970, pp. 199–205.

*Primary Examiner*—William E. Kamm
*Attorney, Agent, or Firm*—Kenyon & Kenyon Reilley Carr & Chapin

[57] ABSTRACT

An improved heart pacemaker of the type which includes a stimulating electrode and a counter electrode, a pulse generator and which has an implantable glucose/oxygen biofuel cell as an energy supply, in which pacemaker the area of the glucose electrode of the biofuel cell is made larger than that of the stimulating electrode and the stimulating electrode is in electrically conductive connection with the glucose electrode and thus at the same potential.

9 Claims, 3 Drawing Figures

PACEMAKER WITH BIOFUEL CELL

BACKGROUND OF THE INVENTION

This invention relates to heart pacemakers in general and more particularly to an improved heart pacemaker using a biofuel cell as the energy supply.

The use of biofuel cells to supply energy or power to a heart pacemaker, the biofuel cell being implanted in the body, is known in the art. In particular, a glucose/oxygen biofuel cell is disclosed in German Offenlegungsschrift No. 2,200,054 and U.S. Pat. No. 3,861,397, respectively. In such biofuel cells the chemical energy of the body substances is utilized to generate the electrical energy required to operate the pulse generator of a heart pacemaker. The pulse generator then stimulates the myocardium to beat by means of electrical pulses transmitted through a stimulating electrode. By using a biofuel cell as the energy supply of the heart pacemaker frequent replacement of the energy source is not necessary as is the case where primary cells such as Zn/HgO or Cd/HgO cells are used. As a result, relatively frequent operations for energy source replacement which are expensive, expose the patient to danger of infection and make demands on hospitals, clinics and physicians are avoided.

Typically the stimulating electrode disposed in the heart is a noble metal electrode with platinum being used in most cases. However, such electrodes generally establish a relatively high potential, e.g. approximately 800 to 900 mV, when measured with respect to an hydrogen electrode in the same electrolyte. This is because they also function as electrocatalysts whereby they assume the potential of an oxygen electrode. However this results in poor blood compatibility. Only electrodes which are negative or slightly positive have good blood compatibility. Relatively high positive potential such as the oxygen potential can lead to blood coagulation. Another disadvantage resulting from a high potential in the stimulating electrode is poor body compatibility. The stimulating electrode has a strong catalytic oxidizing effect on proteins, and in particular on the muscle tissue to which the stimulus is to be transmitted. As a result, the tissue adjacent to the stimulating electrode suffers irreversible damage and is destroyed, i.e. connective tissue capsules are formed. Since the stimuli can only act on healthy tissue some distance away from the electrode a greater amount of energy must be supplied. Furthermore the current density drops off because of this effect since the stimulating electrode is generally of a hemispherical shape. Preferably the stimulation is carried out with a cathodic polarization of the stimulating electrode since the stimulation threshold is more favorably situated for a cathodic stimulating pulse than for an anodic stimulating pulse.

In view of the difficulties mentioned above, it is the object of the present invention to provide a pacemaker which has improved body and blood compatibility.

SUMMARY OF THE INVENTION

The present invention accomplishes these objectives in a heart pacemaker which comprises a stimulating electrode, a counter-electrode, a pulse generator and an implantable glucose/oxygen biofuel cell by making the area of the glucose electrode of the biofuel cell larger than the stimulating electrode and by electrically connecting the stimulating electrode with the glucose electrode so that they are both at the same potential.

By so constructing the pacemaker the stimulating electrode's potential is reduced to a range only about 50 to 200 mV as measured with respect to a reversible hydrogen electrode in the same electrolyte. That is to say, it is reduced to a potential at which good blood compatibility and body compatibility will be expected. Since the geometric area of the stimulating electrode is smaller than that of the glucose electrodes, local currents flowing between the stimulating electrode and glucose electrode due to the stimulating electrode acting as an oxygen electrode because of the material used can not influence the potential of the stimulating electrode in an unfavorable manner. The dimensioning of these two electrodes according to the present invention is further advantageous since it is desirable to keep the stimulating electrode small in order to be able to supply a high current density at the point of stimulation with a relatively small power output. On the other hand, it is necessary that the glucose electrode be as large as possible so that the power delivered by the biofuel cell is in the required range from about 50 to 100 $\mu W$.

In accordance with the present invention it is preferable that the counter-electrode of the pacemaker be designed as a glucose electrode. Through such a design it is at the same potential as the actual glucose electrode and thus approximately at the same potential as the stimulating electrode resulting in only a small polarization loss for the stimulating pulse.

The pacemaker in the present invention may have a plurality of stimulating electrodes with a separate biofuel cell provided as the energy source for each of the stimulating electrodes. In such an embodiment each stimulation electrode will be electrically connected to its associated glucose electrode and will have an area smaller than that of the latter. With such a design the reliability and functional dependability of the heart pacemaker is increased. Furthermore, some patients require stimulation with two electrodes in order to normalize the heart time volume, i.e. to make sure that the heart pumps a sufficient amount of blood per unit time.

Up to the present time pacemakers along with their energy source have generally been implanted in the patient's abdominal or chest area and connected by means of a cable to the stimulating electrode disposed in the heart. It has previously been suggested that a self consuming magnesium or magnesium alloy anode (sacrificial anode) for the pacemaker, having a biogalvanic cell as the energy source, be placed in the body tissue and the cathode, i.e. an oxygen electrode, in the venous blood stream, in particular in the right atrium. The output of a biofuel cell disposed in the body tissue and using exclusive natural body substances as fuel is limited by the diffusion of the energy carriers, i.e. glucose and oxygen, from the body fluid to the respective electrodes, i.e. the glucose and oxygen electrode. As a result, such biofuel cells only are capable of a power density of a few $\mu W/cm^2$. For this reason it is necessary to provide electrode areas of approximately 20 cm$^2$ in order to get the power output of 50 to 100 $\mu W$ required for the operation of the heart pacemaker.

It is particularly advantageous, therefore, to place the biofuel cell of the pacemaker of the present invention in the blood stream. In such a case both electrodes of the biofuel cell are in the shape of cylindrical shells and the oxygen electrode is arranged to be floodable by blood flowing in the blood vessel in which it is implanted. For, the energy carriers glucose and oxygen are present in the blood in a higher concentration than in body tissue and, furthermore, the motion of the blood favors a continuous supply to the biofuel cell. In addition, an arrangement of this nature not only avoids the disadvantages present in previously used models with respect to blood and body incompatibility due to a high potential stimulation electrode, but it also increases the efficiency because longer electrical connecting wires to the stimulating electrode are not needed. The cylindrical design also facilitates introduction into the blood stream. Finally, good hydrodynamic design can prevent eddies from forming in the blood stream which could lead to coagulation.

By placing the biofuel cell in the blood stream power densities can be increased to about 200 to 500 $\mu W/cm^2$. As a result, an electrode area less than 1 $cm^2$ is sufficient to generate the power required for the operation of the pacemaker. In this connection, it should also be noted that the cylindrical design of the biofuel cell used as the energy source for the pacemaker and its placement in the blood stream by itself provides considerable advantages over previously used arrangements even if the glucose electrode is not made larger than the stimulating electrode and connected to the latter. Even without these previously mentioned measures, the placement in the blood stream permits the heart pacemaker to be disposed close to the point of stimulus action increasing the efficiency because long leads are no longer required. Moreover, the operation procedure for implanting the pacemaker is simplified and facilitated because more possibilities of implantation in the body are made available when the biofuel cell is kept to a small size, which is the case when it is implanted in the blood stream. In addition, the operative and therapeutic risk is reduced since only small operative procedures are required, which in some cases may even be carried out under local anesthesia.

The biofuel cell of the present invention possesses rotational symmetry. It is preferably of a cylindrical design or that of an elliptical body of rotation. Using a cylinder 1 cm long and 3 mm in diameter will result in a generated surface of approximately 1 $cm^2$ and thus will provide the required electrode area. A cylinder of this nature may easily be placed in the blood stream. Thus the cylinder may have the shape of a circular cylinder, i.e. its plan view may be circular, but it may also be elliptical or of another shape. Beyond this, the cylinder shell may be curved toward the center line of the cylinder near the end faces of the cylinder resulting in a roughly cigar shaped part, i.e. elliptical body of rotation. A design of this nature has as its advantage that it is hydrodynamically favorable.

With the biofuel cell in the form of a hollow cylinder, the electrodes can be coaxially arranged cylindrical shells with the outer cylinder used, at least in part, as the glucose electrode and the inner cylinder, at least in part, as the oxygen electrode. Such a hollow cylinder is inserted in a vein, i.e. in a blood vessel, such that the blood flows through it. In this way, the fuel mixture containing glucose and oxygen first reaches the oxygen electrode where the oxygen is converted selectively and completely. The glucose passes through the oxygen electrode and a membrane separating the oxygen electrode and glucose electrode and is converted at the glucose electrode. Shielding the glucose electrode by means of the oxygen electrode insures that no oxygen reaches the glucose electrode. This is important because there are at present no suitable electrode materials for oxidizing fuel selectively in the presence of oxygen (see U.S. Pat. No. 3,861,397).

This hollow cylindrical embodiment which is disposed inside a vein has a particular advantage in that the biofuel cell can be firmly localized in the blood stream by fitting it to the diameter of the vein. When the biofuel cell is introduced to the vein, the latter is dilated and the tissue, i.e. the vessel wall, then encloses the biofuel cell firmly. This causes the biofuel cell to penetrate into the tissue, i.e. the hollow cylinder is surrounded in such a manner that the blood stream encounters no edges or corners which could lead to the formation of eddies. It is, however, further advantageous in this embodiment, as will be explained below, to design the ends of the biofuel cell or the faces of the cylinder so as to have a hydrodynamically favorable shape, such as by rounding them off.

It is also possible to design the biofuel cell in the form of a hollow cylinder so that both the inner and outer cylindrical shells are oxygen electrodes, with a glucose electrode between them. Such an embodiment would be placed in the blood stream such that blood flows around and through it. Still more favourable it is to have the biofuel cell in the shape of a hollow cylinder whose faces are closed off and which cylinder is favorably designed in the hydrodynamic sense, i.e. shaped to have a good flow profile by means of the faces of the hollow cylinder being closed off so as to form hemispheres or domes. With such a hollow cylinder, the electrodes of the biofuel cell will once again be designed as coaxially disposed cylindrical shells. In this design the outer shell will, at least in part, form the oxygen electrode and the inner shell, at least in part, the glucose electrode. The hollow cylinder is placed in the heart in such a manner that blood flows around it. Once again, the glucose will reach the glucose electrode from the fuel mixture, i.e. the blood, through the selective oxygen electrode.

This embodiment has as a further advantage the miniaturization not only of the biofuel cell, but of the entire pacemaker. In this embodiment, the stimulating electrode can be disposed at one end of the hollow cylinder and the electrical lead to the stimulating electrode inside the hollow cylinder. This results in the space savings and in the possibility of easily introducing the pacemaker into the heart. It is particularly advantageous if the stimulating electrode is placed at one end of the cylinder and the pulse generator inside the hollow cylinder. Through this design a compact, miniaturized pacemaker is obtained with the entire electronic system, including pulse generator and, if necessary, a voltage transformer housed inside a small energy source. The single compact unit can then be placed in the heart, in a single step. In conventional fashion a voltage doubler may be used instead of a voltage transformer where required. In the disclosed embodiment a means are attached to the other end of the hollow cylindrical unit, i.e. the end opposite the stimulating electrode, to permit easy removal of the pacemaker if necessary.

A miniaturized pacemaker of this nature has as its major advantages an extremely small operative risk and high degree of safety when implanting and, in addition, an extremely high efficiency. Furthermore, the arrangement of the stimulating electrode and counterelectrode close together, both forming part of the compact pacemaker, leads to further energy savings since the current travels only a short distance from the stimulating electrode to the counter-electrode. Furthermore, there is no major resistance within the electrical connecting wires. In contrast to conventional pacemakers which require a space of more than 100 cm³, the pacemaker of the type proposed by the present invention require only a volume on the order of 1 cm³. This is possible not only because the biofuel cell can be sufficiently miniaturized but also because the total electronic system can be miniaturized therewith.

The miniaturization of the biofuel cell necessitates the use of extremely thin, yet highly active and mechanically strong electrodes. Such electrodes cannot or can only inadequately be produced by conventional methods. However, the method described in U.S. patent application entitled "Method For The Manufacture Of An Electrode for Electro-Chemical Cells," Ser. No. 545,404, filed Jan. 30, 1975 is suited for the manufacture of the type of electrodes needed. This method produces electrodes having a Raney noble metal catalyst layer located on a laminar, metallic support structure. The Raney noble metal catalyst layer is obtained by dissolving the inactive component out of a layer of a homogeneous alloy, consisting of at least one of the metals of the platinum group of the periodic table of elements, forming an active component, and at least one of the metal of the iron group of the periodic table of elements, as the inactive component located on the support structure. The alloy should contain at least 65 atom-percent of the inactive component. The starting point for use in the fuel cells of the pacemaker of the present invention can then be a rotationally symmetrical part of this type, in particular a hollow cylinder having a wall thickness of a few tenths of a millimeter.

With regard to the need for a voltage transmformer, it should be noted that stimulation threshold required to stimulate the myocardium ranges between 0.5 and 3V. However, generally a voltage of 5 volts is used for stimulation. Biofuel cells supply a voltage of about 0.5 V so that, when they are used as the energy source for pacemakers, a voltage transformer is generally required unless several cells are connected in series, which requires corresponding additional space. However, where the stimulation threshold can reliably be lowered to under 0.5 V no voltage transformer is required. Such is possible through an optimization of the entire system and particularly, by making the stimulating electrode smaller.

DETAILED DESCRIPTION OF THE PREFERRED EMBODIMENT

Figure 1:
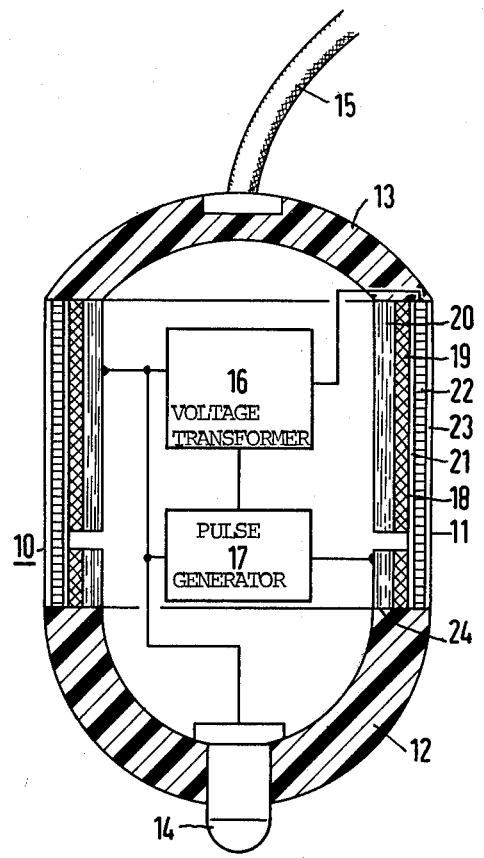
FIG. 1 is a cross section through a first embodiment of the pacemaker of the present invention.

FIG. 1 illustrates schematically on an enlarged scale and in cross section a first embodiment of the pacemaker of the present invention. The pacemaker designated generally as 10 and which will preferably be disposed in the heart is designed with a shape which forms a good flow profile. In essence, the housing of the pacemaker 10 comprises a biofuel cell 11 having diameter diamter and height approximately 6mm in the form of a hollow cylinder with plastic caps 12 and 13 closing the hollow cylinder. Materials used are blood compatible plastics, particularly epoxy resin and silicone resin. The shape of the plastic caps 12 and 13 is that of a dome, i.e. a hemisphere or spherical segment. A stimulating electrode 14 is mounted in the cap 12. The stimulating electrode is a platinum/iridium alloy containing 10 to 20% iridium by weight. The effective area of the stimulating electrode, i.e. the area projecting beyond the cap 12, is essentially in the form of a hemisphere. The hemisphere has a radius of approximately 1 mm resulting in an effective area for the stimulating electrode of approximately 6 mm². Attached to the component 13 is a connection 15 to permit removing the pacemaker from the blood stream. The pacemaker 10 includes conventional electronics including a voltage transformer 16 and a pulse generator 17 both of which are housed inside the hollow cylinder. The biofuel cell 11 is made up of a number of elements. The largest portion of the inner cylindrical shell is in the form of a glucose electrode (anode) 18. The glucose electrode is made up of two layers. An outer Raney-platinum layer 19 is the active layer and is supported by an inner layer 20 of platinum/nickel alloy which is used both for support and for current take off. This anode is prepared using the above described method so that the nickel in a hollow cylinder consisting of a platinum/nickel alloy (atomic ratio Pt:Ni = 1:6) and having a wall thickness of a few tenths of a millimeter is dissolved out of the outer cyliner wall by chemical etching with an inorganic acid such as hydrochloric acid, sulfuric acid or nitric acid or an acid mixture, or by an electro-chemical activation such as a potentiodynamic or potentiostatic treatment, such that there will be a Raney-platinum layer (the outer cylinder wall) with a layer thickness of between 1 and 100 $\mu M$ on top of a layer comprising a platinum/nickel alloy (the inner cylinder wall of the hollow cylinder).

The outer cylinder wall, i.e. the Raney-platinum layer 19, is then covered by a hydrophilic membrane 21 for separating the two electrodes. The membrane 21 may comprise an ion exchange material but preferably will be a hydrogel. The arrangement comprising the glucose electrode 18 and membrane 21 is fitted into a hollow cylinder comprising a silver/aluminum alloy (approximate silver content 20 percent by weight) and having a wall thickness of approximately 100 $\mu M$. The aluminum is then dissolved out of this alloy using a potassium hydroxide solution so that a porous oxygen electrode 22 of Raney silver is obtained. The oxygen electrode 22 is then provided with a hydrophilic membrane 23. The membrane 23, permeable to glucose and oxygen, is used for keeping proteins away from the electrode surface. As mentioned above, suitable materials for the membranes are particularly hydrogels, i.e. polymers produced by means of hydrophilic crosslinking agents; the polymerization takes place in the presence of water and the polymers assume their final swell state during the polymerization. Such polymers are preferably prouced by the polymerization of glycolmethacrylate (methacrylic acid-2-hydroxy ethyl ester) as a monomer with water soluble tetraethyleneglycoldimethacrylate as a crosslinking agent in the presence of more than 45% water. Copolymers containing up to 3% by weight of methacrylic acid or methacrylic acid-2-dimethylaminoethylester may also be used.

The membrane 23 may be applied to the oxygen electrode, example, by immersing the oxygen electrode in a solution of hydrophilic polymer and subsequently drying it. If applicable, crosslinking process may follow to make the polymer insoluble. However, the membrane 23 may also be applied by first providing the oxygen electrode with a porous carrier material, in particular with a thin paper sleeve, and subsequently impregnating it with a solution containing the following ingredients: a monomer to form a polymer, a crosslinking agent and, if applicable, a polymerization catalyst.

The glucose electrode 18 or layer 20 is electrically connected with the stimulating electrode 14. The voltage transformer 16 is also connected to the layer 20 of the glucose electrode 18 and to the oxygen electrode 22. A connection exists between the voltage transformer and pulse generator 17 with the pulse generator having a connection to the stimulation electrode 14 and to a counter electrode 24. Counter electrode 24 is designed as a glucose electrode and is electrically insulated from the glucose electrode 18. The electrodes have approximately the following areas: Oxygen electrode 1.1 cm$^2$, glucose electrode 1 cm$^2$ and counter electrode 0.1 cm$^2$. In operation, the oxygen electrode adjusts itself to a potential of approximately 640 mV each measured against an hydrogen electrode in the same electrolyte. As a result, the cell voltage is approximately 0.5 V. The potential of the stimulating electrode connected to the glucose electrode is approximately 145 mV, thereby being slightly more positive than the potential of the glucose electrode.

As is evident from FIG. 1, the stimulating and counter electrode inside the heart are closely adjacent. This saves electrical energy since the current must travel only a short distance from the stimulating electrode to the counter electrode. This aids even further in miniaturization.

As indicated above and shown on FIG. 1 the inner hollow cylinder of the biofuel cell 11 is divided into two sections with the larger section forming the glucose electrode 18 and the smaller one a counter-electrode 24. Such a division into sections which function as separate electrodes is also advantageously made but a plurality of stimulating electrodes are provided for the pacemaker, each electrode having a separate energy supply. In such a case each stimulating electrode is then connected to a separate glucose electrode.

Figure 2:
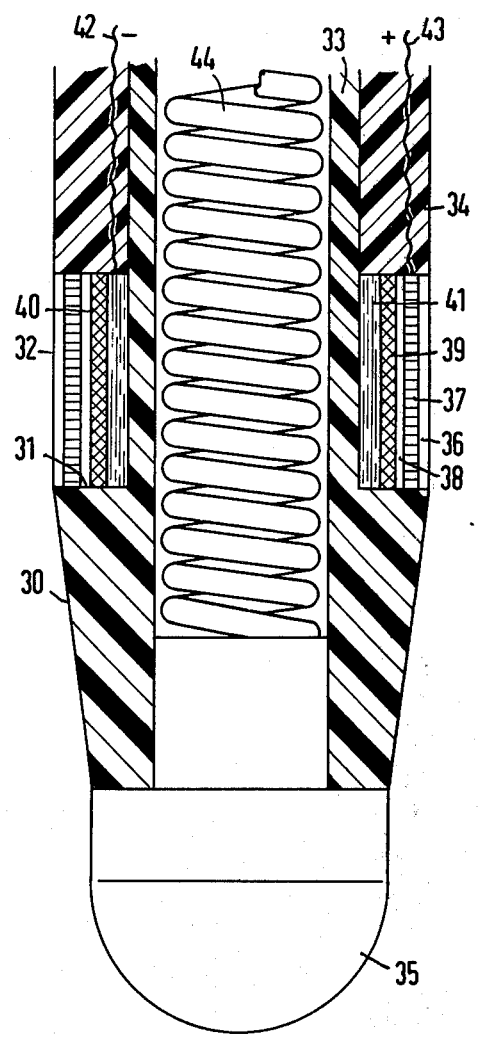
FIG. 2 is a cross section through a portion of a second embodiment of the pacemaker of the present invention.

FIG. 2 illustrates, on an enlarged scale, a cross section through a portion of a second embodiment of the pacemaker according to the present invention. This embodiment is similarly to be disposed in the blood stream with blood flowing around it. A biofuel cell 32 is disposed in a recess 31 of a plastic frame 30. This assembly can be produced by pushing the hollow cylindrical biofuel cell 32 onto a plastic hollow cylinder 33 whose outer cylindrical wall has an enlargement on one end and then pushing on a plastic hollow cylinder 34 of the same diameter as the biofuel cell 32. Hollow cylinder 33 is closed at the enlarged end by the stimulating electrode 35 such as to result in a hydrodynamically favorable profile for the completed assembly. The biofuel cell 32 is designed in the same manner as the biofuel cell of FIG. 1. On its outside it has a hydrophilic membrane 36 resting against the oxygen electrode (cathode) 37. Another hydrophilic membrane 38 separates the oxygen electrode from the active layer 39 of the glucose electrode 40. The second layer 41 of the glucose electrode 40 which is used as a support of the active layer and for taking-off current rests against the plastic hollow cylinder 33. An electrical lead 42 is connected to the anode 40 and an electrical lead 43 to the cathode 37. An electrical lead from the pulse generator to the stimulating electrode 35 is designated as 44.

Figure 3:
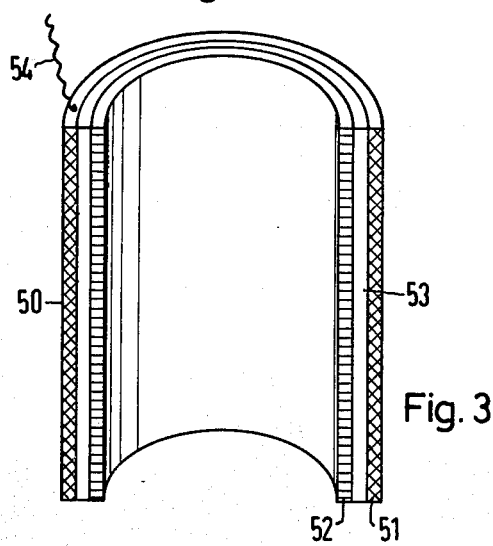
FIG. 3 is a cross section of an embodiment of a biofuel cell for use in a heart pacemaker according to the present invention.

FIG. 3 illustrates, also on an enlarged scale, a schematic cross section through a hollow cylindrical biofuel cell which can be inserted into the blood stream such that blood flows through it. In essence, the biofuel cell 50 comprises two hollow cylinders 51 and 52. The outer hollow cylinder, i.e. cylinder 51 will hug the wall of the blood vessel closely after being implanted and is the glucose electrode. The inner hollow cylinder 52 is the oxygen electrode. The electrodes are separated from each other by a hydrophilic membrane 53. An electrical lead 54 is taken from the glucose electrode and is connected to the lead going to the stimulating electrode in accordance with the present invention. Prior to introduction into the blood vessel, the oxygen electrode is also covered by a hydrophilic membrane. In this embodiment of the biofuel cell both electrodes may be produced by the above described method. Generally, however, other electrode materials may be used such as activated charcoal for the cathode. The nonporous layer which supports the active layer and provides a curent take-off for the glucose electrode produced by the method described above is located between the porous active layer and the wall of the blood vessel. If such is not the case, it is advantageous to cover the porous glucose electrode of the biofuel cells intended for insertion into a blood vessel with a nonporous film to exclude access of oxygen to the glucose electrode by diffusion through the wall of the blood vessel from adjacent body tissue. Otherwise, chemical short circuits could occur at the glucose electrode due to the simultaneous reaction of fuel and oxidizing agent, i.e. glucose and oxygen. Films of body compatible plastics such as epoxy and silicone resin may be used as a nonporous film.

The selection of materials for the membranes must always be governed by the fact that the membranes must be bio-compatible, in particular blood compatible. In addition to the membranes already mentioned, membranes having a polyvinyl alcohol or polyvinyl alcohol/polyacrylic acid base may also be considered. It should be pointed out in closing, that the above described biofuel cell is also suitable as an energy supply for other implanted electrical apparatus in addition to its application in pacemakers. In addition, it may also be used as a glucose sensor.

Thus, an improved heart pacemaker with better miniaturization and which provides improved stimulation has been shown. Although specific embodiments have been illustrated and described, it will be obvious to those skilled in the art that various modifications may be made without departing from the spirit of the invention which is intended to be limited solely by the appended claims.

What is claimed is:

1. In a heart pacemaker which includes a stimulating electrode and counter electrode, a pulse generator and an implantable glucose-oxygen biofuel cell as the energy supply, the improvement comprising a glucose electrode in the biofuel cell which has an area larger than that of the stimulating electrode and wherein the stimulating electrode is electrically connected to the glucose electrode so as to be at essentially the same potential as the glucose electrode.

2. Apparatus according to claim 1 wherein the counter electrode is designed as a glucose electrode.

3. Apparatus according to claim 1, wherein a plurality of identical stimulating electrodes are used and wherein a separate biofuel cell is provided as the energy supply for each of the stimulating electrodes.

4. Apparatus according to claim 1 wherein said biofuel cell is to be disposed in the blood stream and wherein the electrodes of said biofuel cell are in the shape of a cylindrical shell with the oxygen electrode arranged so that it will be flooded by blood.

5. Apparatus according to claim 4 wherein said biofuel cell is shaped as a hollow cylinder, the electrodes of said biofuel cell being coaxially disposed cylindrical shells, the outer cylindrical shell being, at least in part, a glucose electrode and the inner cylindrical shell, at least in part, an oxygen electrode and wherein said hollow cylinder is arranged to be inserted into a blood vessel so that blood can flow through it.

6. Apparatus according to claim 4, wherein said biofuel cells is in the shape of a hollow cylinder with means closing the end faces of said hollow cylinder, said means comprising means shaped to have a hydrodynamically favorable effect, the electrodes of the biofuel cell being cylindrical shells coaxially disposed with the outer cylindrical shell forming, at least in part, an oxygen electrode and the inner cylindrical shell, at least in part, a glucose electrode such that said hollow cylinder can be disposed in the heart in such a manner that blood can flow around it.

7. Apparatus according to claim 6, wherein the stimulating electrode is disposed at one end of said hollow cylinder with the electric lead to the stimulating electrode disposed inside said hollow cylinder.

8. Apparatus according to claim 6, wherein said stimulating electrode is disposed at one end of said hollow cylinder with the pulse generator of said pacemaker inside said hollow cylinder.

9. Apparatus according to claim 8 and further including a voltage transformer inside said hollow cylinder.

* * * * *